United States Patent [19]
Wilson et al.

[11] Patent Number: 5,984,941
[45] Date of Patent: Nov. 16, 1999

[54] TROCAR

[75] Inventors: Jeffrey A. Wilson, Mendon, Mass.; John K. Danks, Delray Beach; Jim Young, Davie, both of Fla.

[73] Assignee: Endoscopic Concepts, Inc., Delray Beach, Fla.

[21] Appl. No.: 09/023,537

[22] Filed: Feb. 13, 1998

Related U.S. Application Data

[60] Provisional application No. 60/036,072, Feb. 13, 1997.

[51] Int. Cl.⁶ ..................................... A61B 17/34
[52] U.S. Cl. ..................... 606/185; 606/128; 606/167; 606/170; 604/264; 604/256
[58] Field of Search .................................. 606/128, 185, 606/167–170; 604/264, 256

[56] References Cited

U.S. PATENT DOCUMENTS

| | | | |
|---|---|---|---|
| 5,248,298 | 9/1993 | Bedi et al. | 604/51 |
| 5,314,417 | 5/1994 | Stephens et al. | 604/264 |
| 5,364,372 | 11/1994 | Danks et al. | 604/256 |
| 5,545,150 | 8/1996 | Danks et al. | 604/256 |
| 5,554,137 | 9/1996 | Young et al. | 604/264 |
| 5,591,192 | 1/1997 | Privitera et al. | 606/185 |
| 5,690,663 | 11/1997 | Stephens | 606/185 |
| 5,709,671 | 1/1998 | Stephens et al. | 604/264 |

*Primary Examiner*—Michael Buiz
*Assistant Examiner*—Lien Ngo
*Attorney, Agent, or Firm*—Miller & Martin

[57] ABSTRACT

A trocar is formed from a cannula and an interfitting obturator for penetrating body cavity walls in laparoscopic and endoscopic surgery. The obturator is provided with an improved piercing tip having a pointed blade with an improved sheath mounting and shield design. Hydrophilic coatings or components are also employed on the shield and cannula to facilitate quicker shield action covering the pointed blade and ease of entry of the cannula tube through the body cavity wall. The sheath and obturator handle and housing assembly may be fabricated as a single plastic piece.

20 Claims, 7 Drawing Sheets

TROCAR

The present application claims priority from the Feb. 13, 1997 filing date of U.S. Ser. No. 60/036,072.

BACKGROUND OF THE INVENTION

The present invention relates to a surgical instrument commonly referred to as a trocar, or an obturator and cannula, often used in laparoscopic or arthroscopic surgery. More particularly, the invention relates to new and improved designs for shields, blade mountings and sheaths especially adapted for flat bladed trocars.

Many surgical procedures are now being performed with the use of trocars and cannulas. Originally these devices were used for making a puncture and leaving a tube to drain fluids. As technology and surgical techniques have advanced, it is now possible to insert surgical instruments through the cannulas and perform invasive procedures through openings less than half an inch in diameter. Previously these procedures required incisions of many inches. By minimizing the incision, the stress and loss of blood suffered by patients is reduced and the patients' recovery times are dramatically reduced.

Surgical trocars are most commonly used in laparoscopic surgery. Prior to use of the trocar, the surgeon will usually introduce a Veress needle into the patient's abdominal cavity. The Veress needle has a stylet which permits the introduction of gas into the abdominal cavity. After the Veress needle is properly inserted, it is connected to a gas source and the abdominal cavity is insufflated to an approximate abdominal pressure of 15 mm Hg. By insufflating the abdominal cavity, pneumoperitoneum is created separating the wall of the body cavity from the internal organs.

A trocar is then used to puncture the body cavity. The piercing tip or obturator of the trocar is inserted through the cannula or sheath and the cannula partially enters the body cavity through the incision made by the trocar. The obturator can then be removed from the cannula and an elongated endoscope or camera may be inserted through the cannula to view the body cavity, or surgical instruments may be inserted to perform ligations or other procedures.

A great deal of force is often required to cause the obturator to pierce the wall of the body cavity. When the piercing tip breaks through the cavity wall, resistance to penetration ceases and the tip may reach internal organs or blood vessels, with resultant lacerations and potentially serious injury. The creation of the pneumoperitoneum provides some free space within which the surgeon may stop the penetration of the trocar. To provide further protection, trocars have more recently been developed with spring loaded shields surrounding the piercing tip of the obturator. Once the piercing tip of the obturator has completely pierced the body cavity wall, the resistance of the tissue to the spring loaded shield is reduced and the shield springs forward into the body cavity and covers the piercing tip. The shield thereby protects internal body organs and blood vessels from incidental contact with the piercing tip and resultant injury. Trocars including various safety shield designs are described in Yoon, U.S. Pat. No. 4,535,773; Moll, U.S. Pat. No. 4,654,030; and Moll, U.S. Pat. No. 4,601,710. An improved piercing tip comprised of a pointed planar blade with an improved safety shield is also the subject of commonly owned U.S. Pat. Nos. 5,364,372 and 5,607,440.

Once the cannula has been introduced into the opening in the body cavity wall, the pneumoperitoneum may be maintained by introducing gas into the abdominal cavity through the cannula. Various seals and valves have been utilized to allow abdominal pressure to be maintained in this fashion. Maintaining abdominal pressure is important both to allow working room in the body cavity for instruments introduced through the cannula, and to provide free space for the puncturing of the body cavity wall by one or more additional trocars as may be required for some procedures.

While the existing planar bladed obturators and cannulas have proven useful, several disadvantages remain. For instance, it is desirable to reduce the force required to cause the piercing tip to penetrate a body cavity wall. Accordingly, designs that minimize the obstacles to penetration of the cannula through the body cavity wall are preferred. In addition, some existing shield mechanisms do not spring forward to cover the obturator tip as quickly as possible and it is necessary that the movement of the shield mechanism not create "pinch points" that could bind with body tissue.

Also, with the current emphasis on cost controls in health care, it is desirable to minimize the cost of medical instruments whenever possible. It has been expensive to manufacture previous flat bladed obturators due to the mounting of the blade in a metal hypotube sheath. Therefore, a need exists for an improved and less expensive apparatus for performing laparoscopic and similar surgical procedures.

SUMMARY OF THE INVENTION

Accordingly, it is the primary object of the invention to provide a safer trocar for piercing body cavity walls.

It is also an object of the invention to provide an improved shield design which will reduce the force required to penetrate a body cavity wall without pinch points.

It is a further object of the invention to provide improved blade mounting on a sheath which permits less expensive manufacture of the sheath and permits the use of less expensive plastic materials in the place of metal.

It is another object of the invention to provide an obturator which may be substantially formed from a single piece of molded plastic.

It is yet another object of the invention to provide an obturator with a sheath mounted blade where the sheath is not exposed outside the cannula.

It is yet a further object to provide a method of mounting a blade in the sheath of a shielded obturator which effectively locks the blade in place, and permits the blade to be sharpened across its entire width.

Accordingly, the present invention provides an obturator with a planar blade and an improved sheath and shield design. To achieve penetration with less force, the outer diameter of the shield is of the same width as the blade, and as is substantially the same as the inner diameter of the cannula. The blade is mounted in the end of a sheath that can be formed as an integral piece with the obturator handle. The shield is received within the sheath and has an intermediate section that can slide in and out of the sheath, and a distal end which always protrudes from the sheath and in its extended position covers the planar blade.

DESCRIPTION OF THE PREFERRED EMBODIMENTS

The invention commonly known as a trocar is comprised of two major components. These are a cannula 13 such as that illustrated in FIG. 1B, and an obturator such as the shielded obturator 12 illustrated in FIG. 1A. The obturator 12 of FIG. 1A and cannula 13 of FIG. 1B are interfitting and as explained below are used together to penetrate a body cavity wall. Once the body cavity wall is penetrated, however, the obturator 12 may be removed and other medical instruments may be introduced into a lumen 19 of the cannula 13.

Referring to FIG. 1B, the cannula 13 includes an outer housing 40, an inner housing 39, and a cannula tube 84 which is secured to and extends from the inner housing 39. In addition, the inner housing 39 is mounted within the outer housing 40. The inner housing 39 contains a gas sealing means such as the illustrated flexible flapper valve 43. The flexible flapper valve 43 will allow the introduction of the obturator sheath 18 of a shielded obturator 12, or other endoscopic instruments (not illustrated) without substantial loss of gas from the body cavity. As shown in FIG. 1B, when no instrument is inserted, the flapper 43 closes against the end plate 37 to maintain the gaseous pressure in the body cavity.

The outer surface of the cannula tube 84 of FIG. 1B is shown with a helically wound thread 49 preferably beginning at a reduced height a short distance from the distal end 68 of the cannula tube 84 and gradually increasing to its full height as it proceeds toward the proximate end 69. At the proximate end 69 of the cannula tube 84, there is a transition to outer housing 40. Along the housing 40 is a gas port 16 which can be connected to a gas supply, not shown, to supply gas through the lumen 19 of the cannula tube 84 into a body cavity to create or maintain pneumoperitoneum.

Figure 1A:
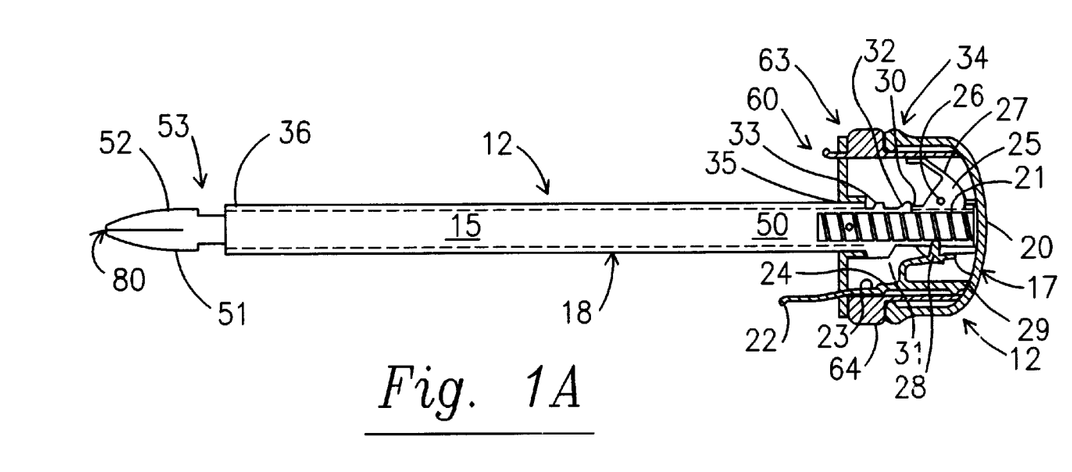
FIG. 1A is a side view in partial cross section of an obturator with an improved shield design and sheath according to the present invention.
Figure 1B:
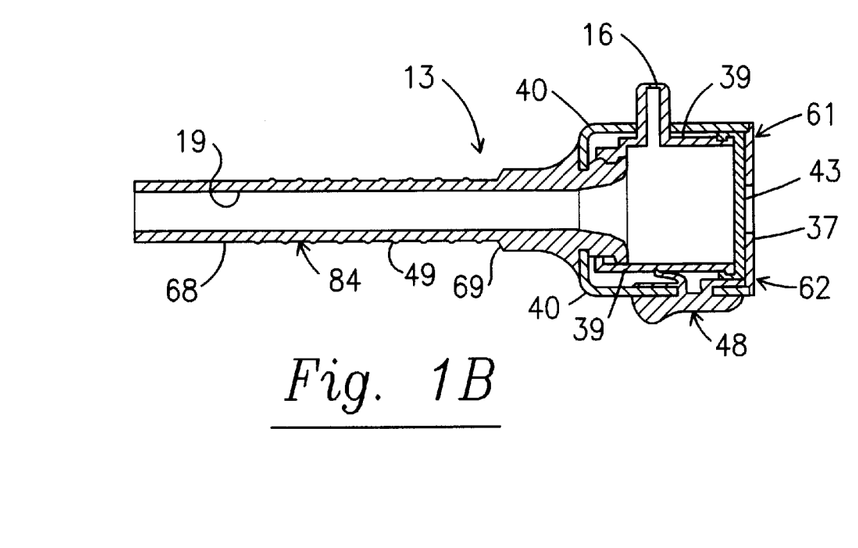
FIG. 1B is a cross sectional side view of a typical cannula for use with the obturator of FIG. 1A.
Figure 6A:
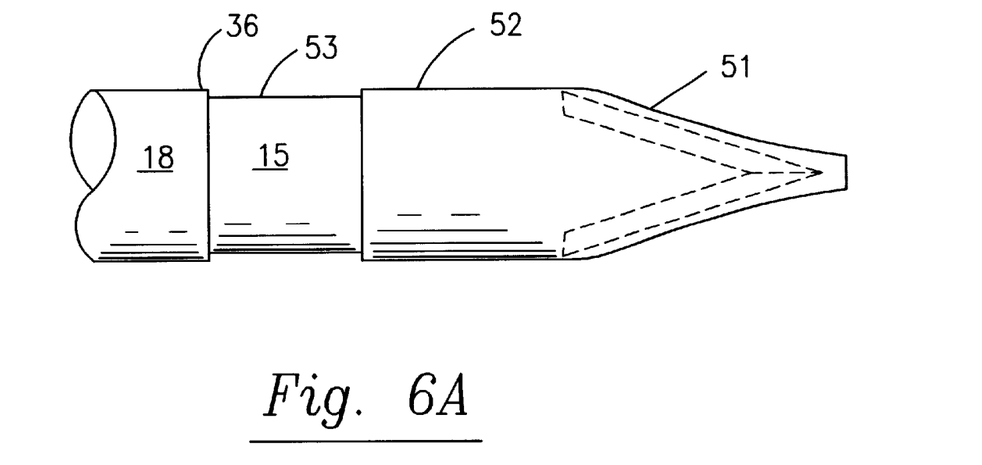
FIG. 6A is an enlarged top view of the improved shield with the obturator removed from a cannula.
Figure 6B:
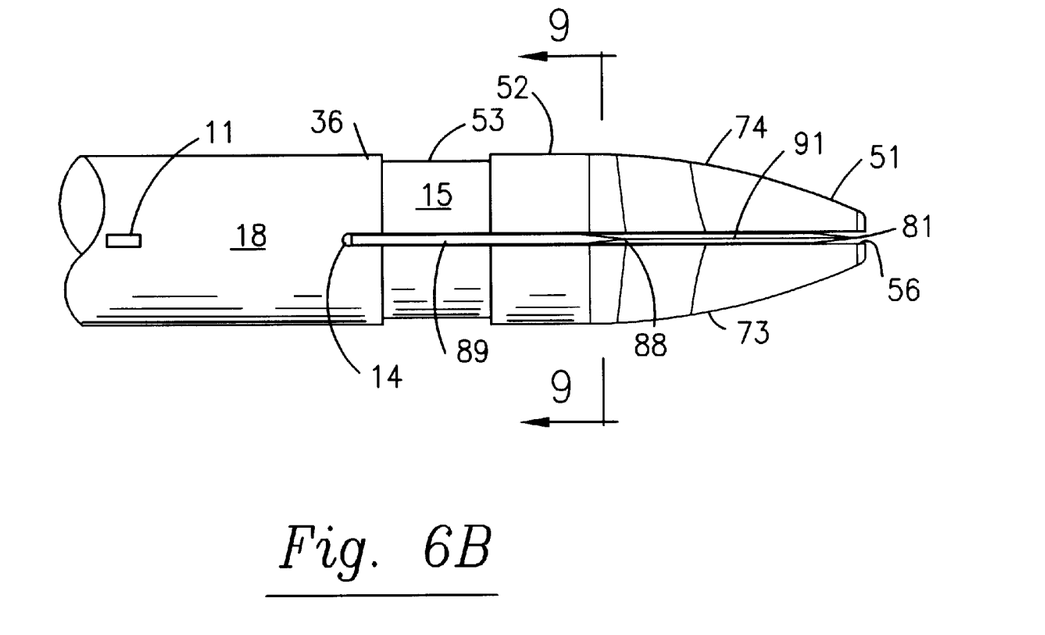
FIG. 6B is a side view of the improved shield of FIG. 6A.
Figure 7:
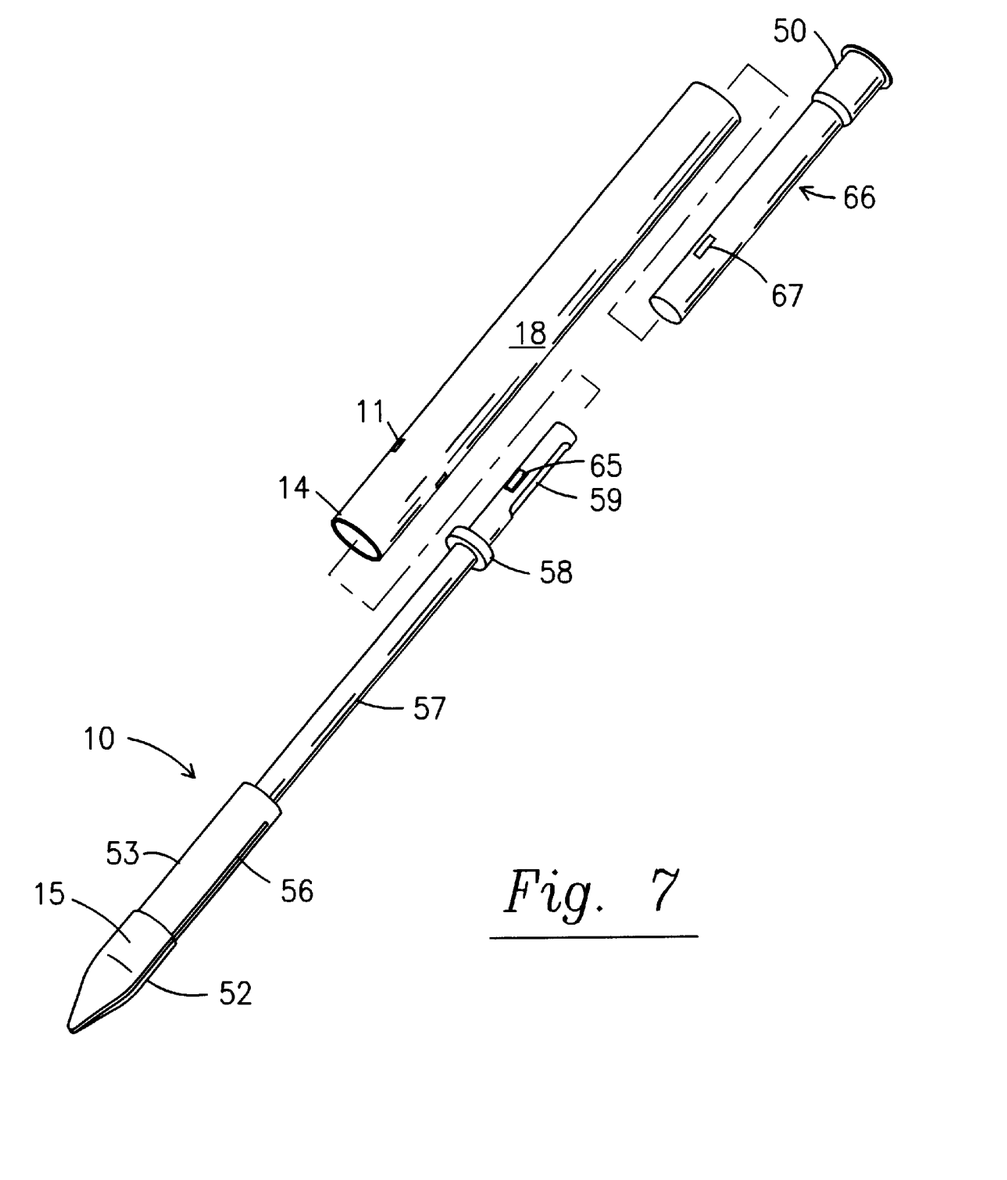
FIG. 7 is a top view of a sheath and two piece shield assembly according to the present invention.
Figures 8A, 9:
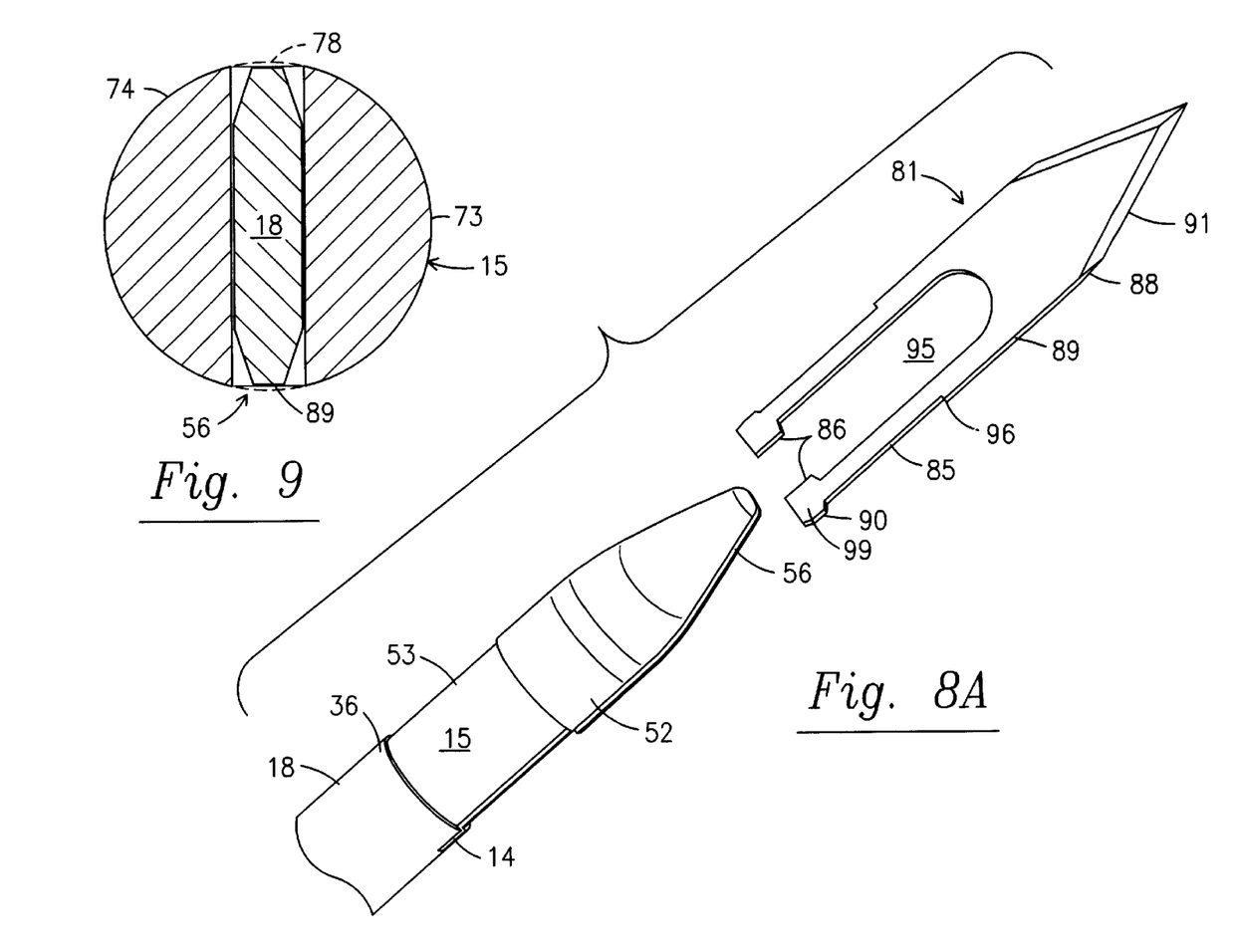
FIG. 8A shows the initial positioning of the planar blade for mounting in the shield and sheath assembly of an obturator.
FIG. 9 shows an enlarged end view cross section of the thickened end portion of the preferred sheath design with the blade in place.

A locking shielded obturator 12 is shown in detail in FIG. 1A. The shielded obturator 12 in FIG. 1A includes an obturator housing 17 which forms a grip or handle. The shielded obturator 12 also includes a hollow obturator sheath 18, the proximal end 35 of which is mounted to the obturator housing 17. The distal end 36 of the obturator sheath 18 is fitted with a piercing tip 80. It should be noted that the distal end 36 may be finished along a substantially straight edge which facilitates the manufacture of this improved sheath design over prior art designs. It also allows the sheath to be molded from plastic rather than cut from a metal hypotube. a preferred sheath design is shown in FIGS. 6 and 7 with several slots to facilitate mounting the piercing tip 80. Housed within the obturator sheath 18 of FIG. 1A is the shield 15, shown in its extended position with the distal end 51 covering the piercing tip 80. The proximal end 50 of the shield 15 is received some distance within the hollow obturator sheath 18 where it is outwardly biased by a biasing means such as the coiled spring 21 interposed between the proximal end 50 of the shield 15 and the inner wall 20 of the obturator housing 17. The shield is sized to fit in this sheath 18 from proximal end 50 up through intermediate section 53. Intermediate section 53 slides in and out of the distal end 36 of sheath 18 when the obturator is used. Beyond the intermediate section 53 of shield 15 is the thickened end portion 52 which has substantially the same diameter as the outer diameter of the sheath 18, except at the sides of the piercing tip as shown in FIG. 9.

Still referring to FIG. 1A, a double action latch 34 for locking the shield 15 in both the extended position and a partially retracted position is illustrated. The latch 34 comprises a biasing means such as the spring 27, a blocking member such as the illustrated pivoting chock 25, an actuator such as the trigger 48, shown in FIG. 1B, and a linkage between the actuator and the blocking member such as the linking member 24. The illustrated latch operates to keep the shield 15 locked in the extended position except when armed or actuated. To lock the shield 15, a solid portion 30 of the pivoting chock 25 engages with a first lug 32 on the proximal end 50 of the shield 15 to prevent the shield 15 from retracting further toward the inner wall 20 of the obturator housing 17 and thereby exposing the piercing tip 80.

In order to permit the shield 15 to be retracted, the latch 34 must first be armed or actuated. To accomplish this, the shielded obturator 12 and cannula 13 must first be interfitted. In FIGS. 1A and 1B, the distal end 22 of the linking member 24 from the shielded obturator 12 is received through opening 62 and engaged in the trigger 48 mounted in the cannula 13. Also a guiding tab 60 from the shielded obturator 12 is received in an opening 61 in the cannula 13. By depressing push buttons 63 and 64, the guiding tab 60 and linking member 24 can be disengaged, allowing for easy separation of the shielded obturator 12 from the cannula 13.

To arm the latch 34 in the embodiment illustrated in FIG. 1A, the distal end 22 of the linking member 24 engages with a trigger 48, shown in FIG. 1B. When the trigger 48 is depressed and pushed forward toward the piercing tip 80, the linking member 24 is likewise pulled forward. A hook 29 on the proximate end of the linking member 24 is engaged in a cradle 28 on the pivoting chock 25. As the linking member 24 is pulled forward, it causes the pivoting chock 25 to turn on its pivot 26 and thereby rotates the solid portion 30 away from the lug 32 on the proximal end 50 of the shield 15. This arms or actuates the obturator 12.

As the trigger 48 continues forward, the linking member 24 also travels forward until a stop block 23 halts further movement. When the stop block 23 halts further movement, the linking member 24 is in measured close proximity to a cam 31 protruding from the proximal end 50 of the shield 15. As soon as the surgeon applies pressure to the trocar 10, the proximal end 50 of shield 15 is pushed back into the housing 17. After the shield 15 is pushed back sufficiently that a second lug 33 on the proximal end 50 of the shield 15 has reached the solid portion 30, the cam 31 on the proximal end 50 of the shield 15 then dislodges the hook 29 of the linking member 24 from the cradle 28 of the pivoting chock 25. A biasing means such as the spring 27 acting on the pivoting chock 25 now causes the solid portion 30 of the pivoting chock 25 to try to return to its original locking position. When the shield 15 is fully retracted, so that the thickened end portion 52 is adjacent the distal end 36 of the sheath 18 at pinch point 55, the pivoting chock 25 cannot return to a locking position. Yet if the shield 15 should extend even partially, so that it is no longer fully retracted, the solid portion 30 of the pivoting chock 25 can engage the second lug 33, and become locked against the shield again becoming fully retracted. This is referred to as a partially locked or semi-protective position. In this fashion the second lug 33 acts as a detent allowing the shield to rachet forward to an extended position.

If the distal end 51 of the shield 15 and piercing tip 80 are properly designed, the partially locked position can provide substantial protection to the patient. With the pointed blade designs discussed in FIGS. 2–4, it is possible to have the shield cover the sharp tip 87 of the blade and allow only the sharpened edges 91 of the blade to remain exposed as shown in FIG. 3. This allows the sharpened edges 91 to continue cutting the body cavity wall but without risk of exposing the sharp tip 87 thus reducing the chance of inadvertent injury during the incision.

Figure 2A:
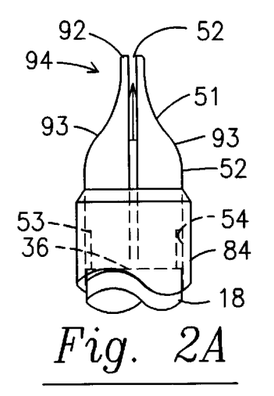
FIG. 2A illustrates a side view of the improved shield design in its fully extended position covering the pointed blade of the obturator extending from the sheath and where the intermediate portion of the shield protrudes from the sheath.
Figures 2B, 3B:
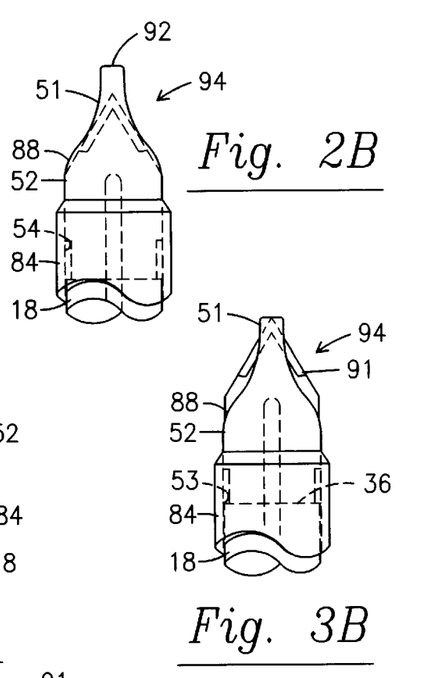
FIG. 2B illustrates a top view of the shield of FIG. 2A.
FIG. 3B illustrates a top view of the shield of FIG. 3A.
Figure 3A:
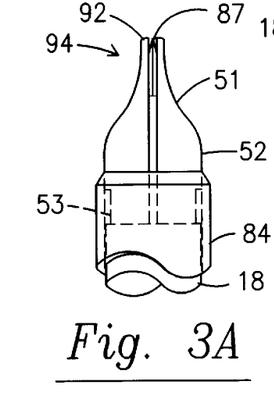
FIG. 3A illustrates a side view of the improved shield design in a partially retracted position exposing only portions of the sharpened edges of the pointed blade of the obturator, but covering the sharp tip of the blade.

When the entire piercing tip 80 of the obturator 18 has passed through the body cavity wall and there is no resistance to the spring loaded shield 15, the shield 15 will spring completely forward to cover the piercing tip 80, as shown in FIGS. 1A and 2, and the pivoting chock 25 will pivot into its original locking position, where the solid portion 30 of the pivoting chock 25 acts to block rearward movement of the first lug 32 on the proximate end 50 of the shield 15. In this fashion, once the body cavity wall has been pierced by the sharp tip 87 and the shield 15 has partially locked, the shield 15 cannot again retract to expose the sharp tip 87 of the piercing tip 80 unless the operating physician uses the trigger 48 to rearm the trocar 10. Once the piercing tip 80 has completely penetrated the body cavity wall and the shield 15 has fully locked, the shield 15 it cannot again retract to oppose any portion of the piercing tip 80. It must be noted that with the complex locking mechanism of FIG. 1A, it is not generally possible to mold the entire obturator housing 17 and sheath 18 from a single piece of plastic. However, for less complex mechanisms, such a non-locking shielded obturator, such unitary molding is possible and effects substantial savings in manufacturing.

Figure 4A:
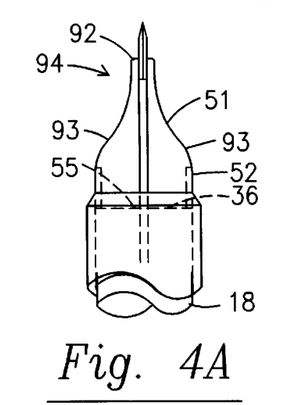
FIG. 4A illustrates a side view of the improved shield design in a fully retracted position exposing the tip and sharpened edges of the pointed blade mounted in the sheath of the obturator and where the intermediate portion of the shield is fully retracted within the sheath.
Figure 4B:
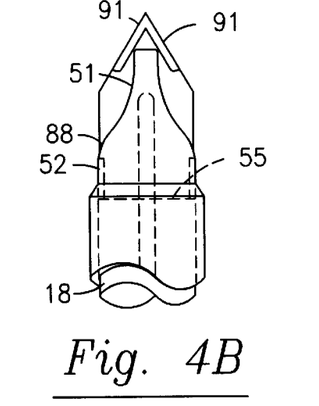
FIG. 4B illustrates a top view of the shield of FIG. 4A.

FIGS. 2–4 illustrate the presently preferred embodiment of the piercing tip 80, which is comprised of a pointed blade 81. The illustrated pointed blade 81 is substantially planar and has a central sharp tip or pointed distal end 87 and straight sharpened edges 91 proceeding from both sides of said distal end 87 to the shoulders 88. In alternative constructions, the blade 81 may have slight convex or concave curves to the sharpened edges 91. The point of the blade may be acute as illustrated or rounded. Other variations of a pointed blade or blades may also be utilized.

As shown in FIG. 2A and 2B, the distal end 51 of the shield 15 used with the illustrated pointed blade is "bottle shaped" or "dolphin nose shaped" in that it has a blunt end 92 at its most distal point which widens slowly at first and then more rapidly so that there is a slight concavity 94 as the distal end 51 of the shield 15 proceeds from the blunt end 92 to a shoulder 93. Proximal of shoulder 93 is the thickened end portion 52 of shield 15 which is of the same diameter as the outside of the sheath 18. Accordingly, it is not possible for the end portion 52 to be received within the sheath 18. When the shield 15 is in its fully protective position as shown in FIGS. 2A and 2B, an intermediate portion 53 of the shield protrudes from the end 36 of the sheath 18. This intermediate portion 53 remains entirely within the cannula tube 84 and because the intermediate portion 53 is narrower than the lumen 19 of the cannula tube 84 by at least the wall thickness of the sheath 18, there is a cylindrical space 53 within the cannula lumen 19 distal of the sheath end 36. As the shield is retracted, this space 53 is reduced and ultimately eliminated when the thickened end portion 52 of the shield 15 is adjacent to the distal end 36 of the sheath 18. This joining of the thickened end portion 52 and distal sheath end 36 creates a pinch point 55. However, because the pinch point 55 is within the cannula tube 84, it cannot pinch or bind with a patient's tissue.

As shown in FIGS. 3A and 3B, when the shield end 51 is of this shape, it is possible for the blunt end 92 to cover the pointed distal end 87 of the blade 81 so that no additional penetration is possible, while still leaving portions of the sharpened edges 91 exposed. In this fashion, when the pointed distal end 87 of the blade 81 has penetrated the body cavity wall, but before the blade 81 is entirely through the wall, the blunt end 92 of the shield can move forward and be partially locked while still allowing the sharpened edges 91 of the pointed blade 81 to expand the incision in the body cavity wall so that the obturator and cannula may be introduced to comminute with the body cavity.

Figure 5A:
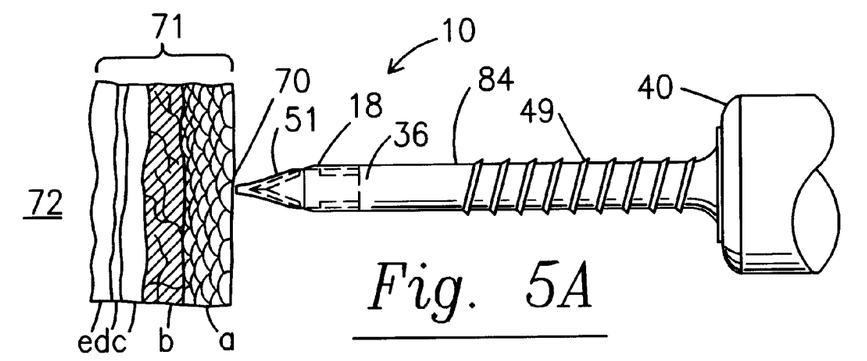
FIGS. 5A through 5D show, in sequential diagrammatic sectional views, an embodiment of the present invention as used to puncture a body cavity wall of a patient.
Figure 5B:
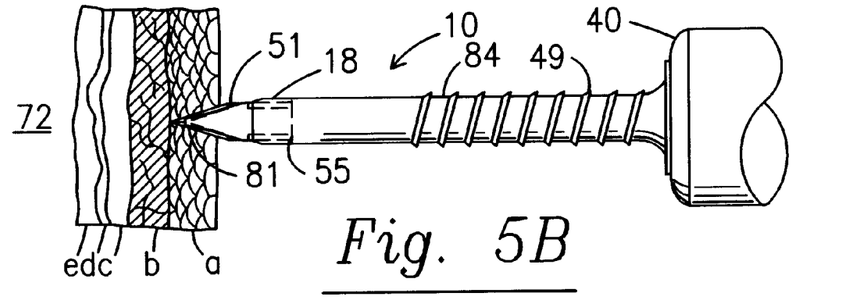

FIGS. 5A through 5D illustrate the piercing tip 80 and shield end 51 of the trocar 10 formed from the obturator 12 and cannula 13 of FIGS. 1A and 1B in use. In FIG. 5A, a small incision 70 is made in the surface of the skin or epidermis "a" of the body cavity wall 71 of a patient. The piercing tip 80, in this case the pointed blade 81, of the trocar 10 with extended shield 51 may then be placed against the incision 70 as shown. When the trocar 10 is in this position, it may be armed or actuated by depressing the trigger 48 (shown in FIG. 1A) and sliding the trigger 48 forward as explained above. When manual force is applied to the obturator housing 17 which forms the trocar handle (shown in FIG. 1A) pushing the trocar to the left, the resistance of the body cavity wall 71 holds back the distal end 51 of the shield 15 and the pointed blade 81 is exposed as shown in FIG. 5B. At this point, the thickened end 52 of the shield 15 is adjacent to the distal end 36 of the sheath 18, at pinch point 55 within the cannula tube 84. The pointed blade 81 then slices through the dermis "a" and subcutaneous tissue including fat cells, muscle, and facia, depicted as "b," "c," "d" and "e" in FIGS. 5A–5D. The various layers of the body cavity wall 71 vary depending upon the cavity being pierced, but in general, the layers of facia are particularly resistant to penetration.

Figure 5C:
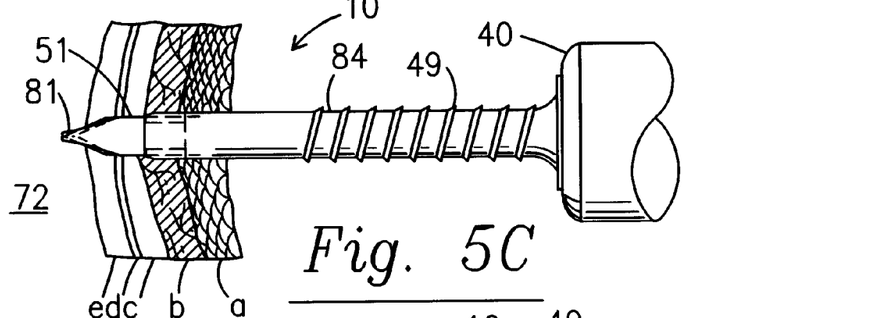

In FIG. 5C, immediately after the sharpened tip 87 of the pointed blade 81 has penetrated the innermost layer "e" of the body cavity wall 71, the blunt end 92 of the distal end 51 of the shield 15 is forced forward through the incision 70 by the bias of the coil spring 21. When the shield 15 reaches this partially retracted position and the preferred double action latch 34 of the obturator 12 illustrated in FIG. 1A is used, the shield 15 will lock so that it cannot be retracted to again expose the sharp tip 87 of the pointed blade 81, yet the shield 15 permits the sharp edges 91 of the blade 81 to continue cutting. This is a semi-protected shield position. At this juncture, the cylindrical space 54 within the cannula tube between the distal end 36 of the sheath 18 and the thickened shield end 52 is only approximately half the length it reaches when the shield 18 is completely forward in the safety position. In this partially locked or semi-protected position the interior of the body cavity 72 and organs, blood vessels and other anatomical structures are protected against puncture by the sharp end 87 of the blade 81.

Figure 5D:
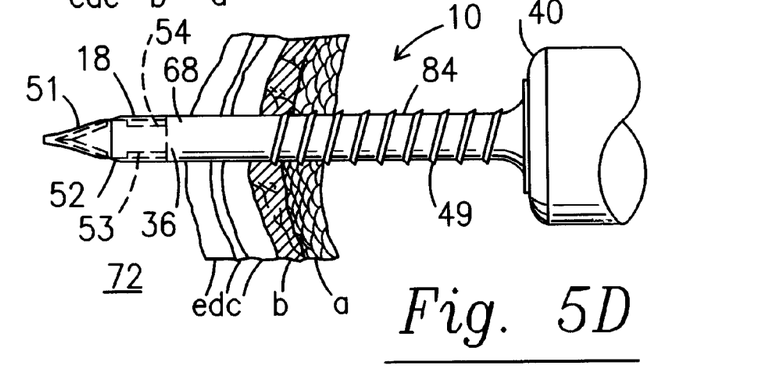

FIG. 5D shows that the shield end 51, the obturator sheath 18, and the distal end 68 of the cannula tube 84 all proceed through the incision 70 in the body cavity wall 71 as manual force continues to be applied to the trocar 10. Just as the shoulder 93 of the distal end 51 of the shield 15 passes through the inner layer "e" of the body cavity wall 71, the resistance of the body cavity wall 71 is significantly reduced and the shield 15 is pushed to its fully extended position with the distal end 51 covering the pointed blade 81. This action completely protects the interior of the body cavity 72 immediately after the full penetration of the pointed blade 81 through the body cavity wall 71 and protects organs, blood vessels and other anatomical structures from incidental contact even with the sharpened edges 91 of the blade 81. Simultaneously with the full extension of the shield 15 into its protective position covering the pointed blade 81, the pivoting chock 25 engages the first lug 32 on the proximate end 50 of the shield 15, which prevents the shield 15 from being retracted to expose the pointed blade 81 until the trocar 10 is again actuated by depressing and moving the trigger 48 forward.

It will be observed that the thickness of the penetrating obturator increases smoothly along pointed blade 81 and distal shield end 51 to the diameter of the thickened end portion 52 of the shield 15. This diameter is substantially the same as the diameter of the cannula lumen 19. As a result, the only step up in diameter for the entry of the trocar through the body cavity wall 71 is the thickness of the cannula tube 84. Prior art designs of sheath mounted blades such as U.S. Pat. No. 5,364,372 had the sheath protrude beyond the distal end 68 of cannula tube 84 and required a step up to the diameter of the sheath 18 and a subsequent step up to the diameter of the cannula tube. The new design therefore reduces resistance to penetration of the body cavity wall.

In order to further improve the performance of the shield 15 in moving forward through the body cavity wall, it is possible to either mold the shield 15 or shield end 51 from a hydrophilic plastic or to coat the shield with a hydrophilic coating. By providing the shield end 51 with appropriate hydrophilic properties, the shield end 51 can be dipped in a wetting solution, usually of water or an appropriate alcohol solution, and the shield end 51 will then have a lower coefficient of friction and will more easily slide through the incision 70 in the body cavity wall 71 to cover the piercing tip 80. Appropriate coatings or compounds must be substantially nonreactive with respect to living tissue and non-thrombogenic when in contact with blood. Appropriate hydrophilic coatings would include polyvinylpyrrolidone-polyurethane or polyvinylbutyrol interpolymers as described in U.S. Pat. Nos. 4,100,309 and 4,119,094. Appropriate molding compounds, which could alternatively also be applied as coatings, include hydrophilic polymer blends with thermoplastic polyurethane or polyvinylbutyrol and hydrophilic polyvinylpyrrolidone or other poly(N-vinyl lactans) as described in U.S. Pat. Nos. 4,642,267 and 4,847,324. An appropriate hydrophillic coating will reduce the coefficient of friction for stainless steel by over 60% and can reduce the coefficients of friction for plastics by over 90%. With the use of hydrophillic plastics for the shield 50 and cannula tube 84, and the placement of the sheath 18 completely within the cannula tube, only the very low coefficient of friction plastics need contact tissue.

The same hydrophilic coatings or compounds may also be used in the cannula 13 which will facilitate the entry of the distal end 68 of the cannula 13 into the incision made by the obturator 12. Although the sharpened blade 81 does not provide substantial resistance, some minor improvement might also be achieved by applying a hydrophillic coating to this blade 81.

FIGS. 6A and B are top and side views of a preferred embodiment of the distal tip of a bullet headed obturator according to the present invention. Thickened shield portion 52 covers all of the sharpened surfaces of pointed blade 81. Said blade 81 being received within slot 56 of shield 15. Although not shown, slot 56 continues up from the distal end of the shield at least to a point past slot 11 on sheath 18. It will be seen that an unsharpened flat section of section 89 of blade 81 is received within the guide slot 14 on sheath 18 to stabilize blade 81. Slot 56 divides distal end 51 of shield 15 into separate upper portion 74 and lower portion 73.

Figure 8B:
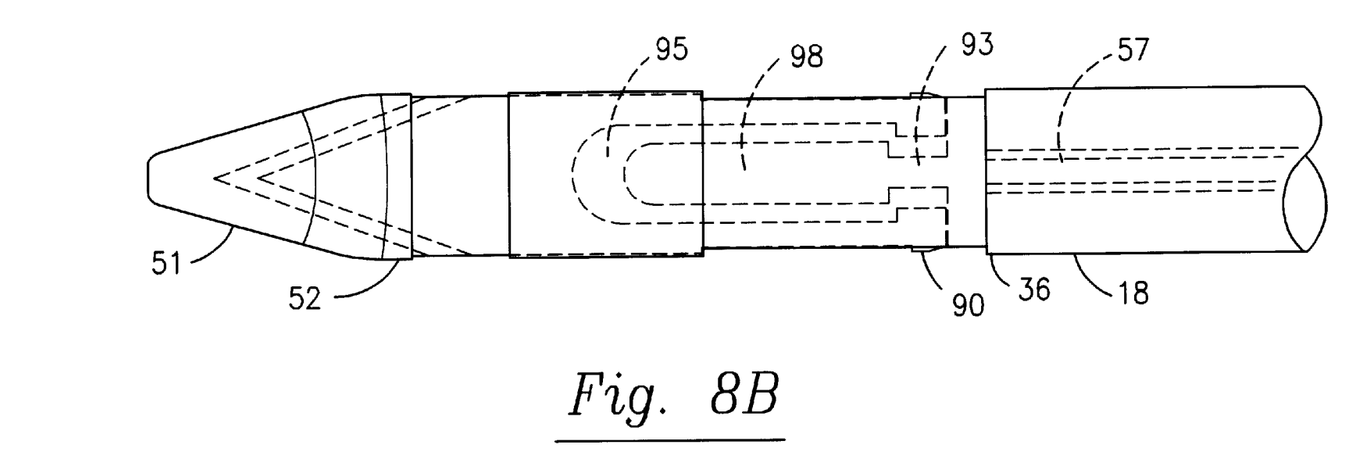
FIG. 8B shows the mounting of the blade in the sheath.
Figure 8C:
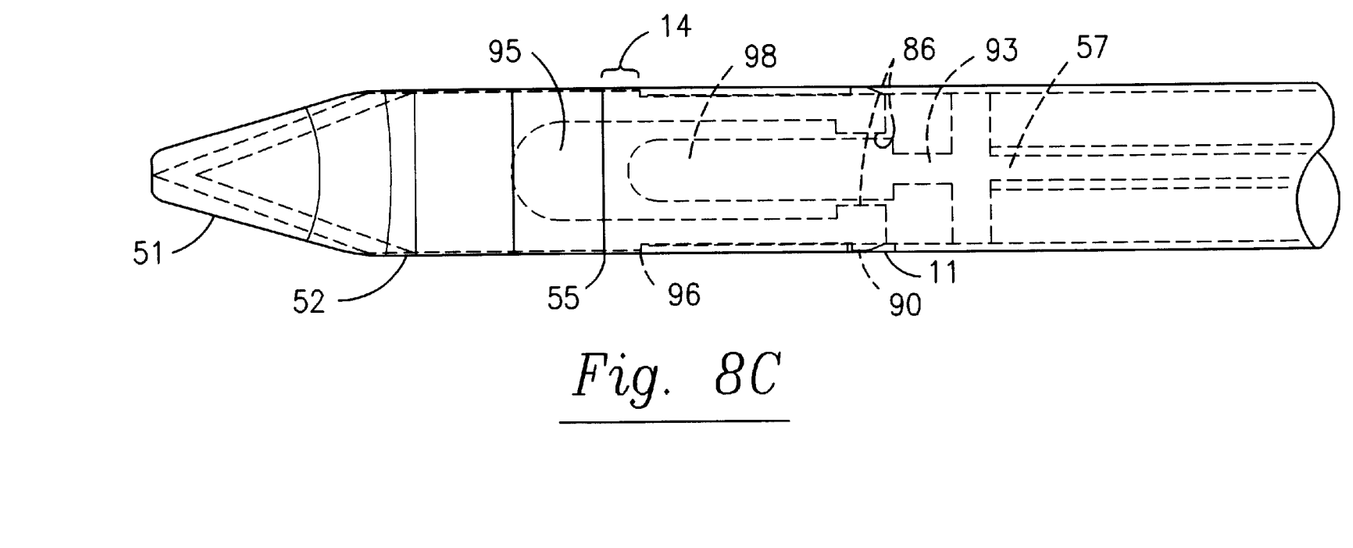
FIG. 8C shows the locking action of the preferred shield design to prevent the blade from disengaging from the sheath.

Continuing onto FIGS. 8A through 8C, a method of mounting blade 81 in shield 15 and obturator 18 is shown. The preferred blade 81 has sharpened edges 91 at the distal end proceeding to shoulder 88. Thence the blade has flattened side portions 89 proceeding proximally toward shoulder 96 and thinned or indented leg portions 85 to foot 99. On the outward side of foot 99 is protrusion 90 and on the inward side of each foot 99 is an inward facing tab 86.

This blade 81 is slipped into slot 56 of shield 15. In the cross sectional view of FIG. 8B, it will be seen that the bomb shaped channel 95 formed between the legs of blade 81 is designed to fit over a protrusion such as a connecting bridge composed of thicker distal section 98 and narrower proximal section 97 wherein such bridge connects the upper part 74 and lower part 73 of the narrowed portion 53 of shield 15. In some circumstances, the bridge 98 may even connect proximal upper and lower portions of thickened shield end 52. When the blade 81 is positioned on shield 15 as shown in FIG. 8B, the shield and blade assembly is inserted into sheath 18. When fully inserted, blade shoulders 96 are received in slots 14 at the distal end 36 of the sheath 18 as shown in FIG. 8C. In addition, the outward directed tabs 90 on feet 99 of shield 81 engage in slots 11 thereby mounting the blade in the sheath 18.

Furthermore, in the preferred embodiment of the bullet headed obturator, after the blade 81 is mounted in sheath 18, the shield 15 is allowed to continue rearward slightly so that thickened bridge portion 98 comes between inward facing tabs 86 on feet 99 of blade 81. The clearance between this thickened portion 96 and the inward facing tabs 86 is limited so that tabs 90 cannot be accidentally disengaged from slots 11 on sheath 18. This provides a valuable safety precaution against the accidental loosening of the blade 81.

In a preferred embodiment as shown in FIG. 7, the shield 15 consists of a distal segment 10 and a proximal segment 66. Rearward of the thickened, bullet headed shield portion 52 and narrowed portion 53 extends a post 57 on which is mounted guide disk 58 to facilitate the alignment and movement of shield 15 within the interior of sheath 18. At the proximal portion of distal shield segment 10 is protruding tab 65 and a compression slot 59. After distal shield portion 10 has been received within sheath 18, this proximal segment with tab 65 is at the proximal end of the sheath. Proximal shield portion 66 is then mated with distal shield portion 10 as by guiding tab 65 into the proximal shield portion 66 until it mates with slot 67. The mating of proximal shield portion 66 to distal shield portion 10 prevents the distal shield portion 10 from moving into the position of FIG. 8B that would permit disengagement of blade leg tabs 90 from slots 11 of the sheath 18. Instead, the most distal position that can be assumed by shield 15 is that shown in FIG. 8C where the distal shield portion completely covers blade 81 but the thickened bridge portion 98 prevents inward movement of the feet 99 of shield 81. The proximal end 50 of proximal shield portion 66 is received within the obturator housing 17 and biased as previously described.

One further observation on the width of 81 is in order and is depicted in FIG. 9. This illustration shows a cross section end view of the thickened end portion 52 of a preferred shield design near the shoulder 88 of blade 81. FIG. 9 shows the upper shield portion 74 and lower shield portion 73 with blade 81 mounted in slot 56 between the two shield portions 74, 73. In order for the shield 15 to cover all of the sharpened portion 91 of blade 81, the blade 81 and shield 15 do not form an exact circle. For manufacturing purposes, it is desirable that sharpened portion 91 of blade 81 be permitted to extend completely to shoulder 88 of the blade. Because there is sharpened portion 91 at the very shoulder 88 of the blade, the edge of the blade cannot extend past the width of the shield 15. Accordingly, the flattened edge portions 89 of blade 81 forms tangents between the almost semi-circular upper 74 and lower 73 shield portions. This leaves a small area 78 between the shoulder 88 and side 89 of blade 81 which will provide clearance between the blade side 89 and the interior lumen 19 of cannula 13 (shown in FIG. 1B). Although such a gap would frequently be thought undesirable as it might create a place where tissue would catch during surgical procedures, this has not proven the case, and providing the clearance area 78 between blade 81 and cannula lumen 19 results in a safer blade and shield design.

Numerous alterations of the structures herein described will suggest themselves to those skilled in the art. It will be understood that the details and arrangements of the parts that have been described and illustrated in order to explain the nature of the invention are not to be construed as any limitation of the invention. All such alterations which do not depart from the spirit of the invention are intended to be included within the scope of the appended claims.

We claim:

1. A shielded obturator comprising:
   a. an obturator sheath having an inner lumen, a distal end and a proximate end;
   b. a handle mounted to the proximate end of said obturator sheath;
   c. a pointed blade on the distal end of the obturator sheath;
   d. a shield slidably mounted relative to the obturator sheath and having a thickened end portion of diameter greater than the inner lumen of said sheath, an intermediate portion relatively narrower than said thickened end portion and a proximal portion; and
   e. a biasing means tending to bias the shield into an extended protective position.

2. The shielded obturator of claim 1 wherein the distal end of the sheath has a substantially straight edge.

3. The shielded obturator of claim 1 wherein said thickened end portion of the shield covers the pointed blade in the extended protective portion, and at least a part of said thickened end portion end is provided with a hydrophillic coating.

4. The shielded obturator of claim 1 wherein the pointed blade is substantially planar and comprises a sharpened point end, a first sharpened edge proceeding from the sharpened point end to a first shoulder, and a second sharpened edge proceeding opposite the first sharpened edge to a second shoulder.

5. The shielded obturator of claim 4 wherein the shield is of cylindrical shape and is slidably mounted within the obturator sheath, said shield having a proximal end received within the obturator handle, and a distal end having a channel of sufficient depth and width to receive the pointed blade within said distal end of the shield.

6. The shielded obturator of claim 5 in which the distal end of the shield has a blunt end and proceeds along a concave curve to a shoulder, said shoulder being of substantially the same width as the obturator sheath.

7. The shielded obturator of claim 6 wherein the distal end of the shield is provided with a hydrophillic coating.

8. The shielded obturator of claim 1 wherein the pointed blade has proximally oriented legs which engage with the obturator sheath.

9. The shielded obturator of claim 8 wherein the shield has a protrusion extending between said proximally oriented legs of the pointed blade.

10. A shielded obturator comprising:
    (a) an obturator sheath having a distal end and a proximal end;
    (b) a handle on the proximate end of said obturator sheath;
    (c) a pointed blade on the distal end of the obturator sheath;
    (d) a shield slidably mounted relative to the obturator sheath and further comprising a forward segment which extends from the distal end of the obturator sheath and an interlocking rear segment which proceeds proximally and is biased in the distal direction.

11. The shielded obturator of claim 10 wherein the forward segment of the shield has a thickened distal end portion.

12. The shielded obturator of claim 10 wherein the pointed blade is substantially planar comprising a sharpened point end, a first sharpened edge proceeding from the sharpened point end to a first shoulder, and a second sharpened edge proceeding opposite the first sharpened edge to a second shoulder.

13. The shielded obturator of claim 10 wherein the forward segment of the shield has a proximal portion of cylindrical shape slidably mounted within the obturator sheath.

14. The shielded obturator of claim 11 wherein the thickened distal end portion has a slot in which the pointed blade is received when the shield is positioned in the distally extended protective position.

15. The shielded obturator of claim 11 wherein the thickened distal end portion has a contour with a blunt distal end and proceeds proximally along a concave curve to a shoulder having substantially the same width as the sheath.

16. The shielded obturator of claim 10 wherein the pointed blade has proximally oriented legs which engage with the sheath and the shield has a protrusion which extends between the proximally oriented legs of the pointed blade.

17. A trocar comprising a cannula having a cannula tube with an interior lumen and an obturator having:
   (a) an obturator sheath having a distal and a proximate end;
   (b) a handle mounted to the proximate end of said obturator sheath;
   (c) a pointed blade at the distal end of the obturator sheath;
   (d) a shield slidably mounted relative to the obturator sheath; and
   (e) a biasing means tending to bias the shield distally into an extended protective position;
   Such that when the obturator is interfitting with the cannula, the distal end of the obturator sheath is entirely contained within the interior lumen of the cannula tube.

18. The trocar of claim 17 wherein the shield has a thickened distal end portion substantially the same width as the interior lumen of the cannula tube.

19. The trocar of claim 17 wherein the shield comprises a forward segment which extends from the distal end of the obturator sheath and an interlocking rear segment which proceeds proximally toward the biasing means.

20. The trocar of claim 17 wherein the pointed blade is substantially planar and comprises a sharpened point end, a first sharpened edge proceeding from the sharpened point end to a first shoulder, and a second sharpened edge proceeding opposite the first sharpened edge to a second shoulder.

* * * * *